United States Patent [19]

Weider et al.

[11] Patent Number: 5,274,114

[45] Date of Patent: Dec. 28, 1993

[54] PREPARATION AND USE OF 3, (4)-SUBSTITUTED PYRROLIDINES AS CATALYSTS FOR THE POLYISOCYANATE POLYADDITION PROCESS

[75] Inventors: Richard Weider, Leverkusen; Uwe Scholz, Cologne; Andreas Ruckes, Leverkusen, all of Fed. Rep. of Germany

[73] Assignee: Bayer Aktiengesellschaft, Leverkusen, Fed. Rep. of Germany

[21] Appl. No.: 834,014

[22] Filed: Feb. 10, 1992

[30] Foreign Application Priority Data

Feb. 17, 1991 [DE] Fed. Rep. of Germany ....... 4104870

[51] Int. Cl.$^5$ .................. C07D 487/00; C07D 487/02
[52] U.S. Cl. ..................................... 548/453; 548/408; 548/418; 548/421; 548/428; 548/531; 548/532; 548/535; 548/536; 548/538; 548/560; 548/570; 502/167
[58] Field of Search ............... 548/408, 418, 421, 428, 548/453, 531, 532, 535, 536, 538, 568, 570; 502/167

[56] References Cited

U.S. PATENT DOCUMENTS

| | | | |
|---|---|---|---|
| 2,826,588 | 3/1958 | Feldkamp et al. | 548/531 |
| 3,318,908 | 5/1967 | Swidinsky et al. | 548/518 |
| 3,544,590 | 12/1970 | Kittleson | 558/405 |
| 4,563,484 | 1/1986 | Jachimowicz | 521/129 |
| 4,992,461 | 2/1991 | Zabrowski et al. | 548/453 |

FOREIGN PATENT DOCUMENTS

| | | | |
|---|---|---|---|
| 255908 | 2/1988 | European Pat. Off. | |
| 296560 | 12/1988 | European Pat. Off. | |
| 393607 | 10/1990 | European Pat. Off. | |
| 0038782 | 11/1971 | Japan | 548/531 |
| 3051370 | 3/1988 | Japan | 548/531 |
| 1338275 | 11/1973 | United Kingdom | |

OTHER PUBLICATIONS

Bull. Soc. Chem. Japan, 60, pp. 4079–4090 (1989) Tsuge.
Chem. Abstracts; vol. 56; 1962; 14233d.
Chem. Abstracts; vol. 61; 1964; 1833f.
Chem. Abstracts; vol. 66; 1967; 75861c.
J. Heterocyclic Chemistry, vol. 25, No. 6, 1988, pp. 1665–1673, F. Orsini et al., "1,3-Dipolar Cycloadditions of Azomethine Ylides with Dipolarophiles. II. Synthesis of Pyrrolizidines".
Gazz. Chim. Ital., vol. 115, No. 10, 1985, pp. 569–571, M. Forte et al., "Synthesis of Pyrrolizidines and 1-Oxapyrrolizidines from Proline".
Chemical Abstracts, vol. 71, No. 13, Sep. 29, 1969, Abstract No. 61109E.
Chemical Abstracts, vol. 101, Sep. 10, 1984, Abstract No. 90743A.
Patent Abstracts of Japan and JP-A-62 072 660 (Dainippon Pharmaceutical Co., Ltd.) Apr. 3, 1987.
Helv. Chim. Acta, vol. 64, No. 7, 1981, pp. 2203–2218, R. Achini, "Synthesis of Phenyl- and Benzyl-Substituted Pyrrolidines and of a Piperidine by Intramolecular C-Alkylation Synthons for Tricyclic Skeletons".
Heterocycles, vol. 23, No. 3, 1985, pp. 653–659, J. Chastanet, G. Roussi, "A New Route to Hexahydropyrrolizine Derivatives Via Nonstabilized Ylide Generated from N-Methylpyrrolidone N-Oxide".
J. Org. Chem., vol. 50, No. 16, 1985, pp. 2910–2914, J. Chastanet, G. Roussi "N-Methylpiperidine N-Oxide as a Source of Nonstabilized Ylide: A New and Efficient Route to Octahydroindolizidine Derivatives".
Synthesis, 1980, pp. 811–812, T. Asai et al., "New Methods and Reagents in Organic Synthesis, 7, alpha-Alkylation of Benzylamine Under Phase-Transfer Catalyzed Conditions".
Bull. Soc. Chem. Soc. Japan, 60, pp. 4079–4090 (1989).

Primary Examiner—John Kight, III
Assistant Examiner—Rachel Johnson
Attorney, Agent, or Firm—Joseph C. Gil; Richard E. L. Henderson

[57] ABSTRACT

This invention relates to the preparation of 3- and/or 4-substituted pyrrolidine catalysts corresponding to formula (I)

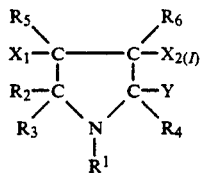
wherein $R_1$, $R_2$, $R_3$, $R_4$, $R_5$, $R_6$, $X_1$, $X_2$, and Y have the meanings described for formula (I) and to use of such catalysts in the polyisocyanate polyaddition process.
1 Claim, No Drawings
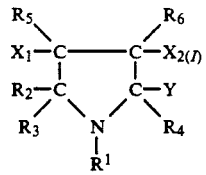
wherein $R_1$, $R_2$, $R_3$, $R_4$, $R_5$, $R_6$, $X_1$, $X_2$, and Y have the meanings described for formula (I) and to use of such catalysts in the polyisocyanate polyaddition process.
1 Claim, No Drawings

PREPARATION AND USE OF 3, (4)-SUBSTITUTED PYRROLIDINES AS CATALYSTS FOR THE POLYISOCYANATE POLYADDITION PROCESS

BACKGROUND OF THE INVENTION

This invention relates to the use of 3- and/or 4-substituted pyrrolidines as catalysts for the manufacture of products by the polyisocyanate polyaddition process. These catalysts may be used as substitutes or in combination with known urethane catalysts, such as 1,4-diazobicyclo[2.2.2]octane (DABCO) for the production of rigid or flexible polyurethane foams and numerous other polyurethane products. The term "polyurethane products" as used herein is to be understood to include all products of reaction of polyisocyanates with compounds having at least two isocyanate-reactive hydrogen atoms; that is, the term polyurethane is used to denote, for example, pure polyurethanes, polyurethane polyureas, and pure polyureas.

The rate of the reaction between isocyanate groups and compounds containing isocyanate-reactive hydrogen atoms is influenced not only by the temperature of the starting products and their structure but particularly also by the use of suitable catalysts. In practice, bases (for example, tertiary amines such as triethylamine) are used mainly as nucleophilic catalysts, whereas organometallic compounds (for example, tin carboxylates such as tin(II) octoate) are used mainly as electrophilic catalysts. The use of Lewis acids together with Lewis bases, which is normally characterized by synergistic effects, is state of the art. It is also known, however, that amines are used as the only catalyst for numerous purposes. Among the large number of known amine Catalysts (see Ullmann 4th Edition and Kunststoffhandbuch Volume VII, Polyurethane, Hansen-Verlag, Munich (1983)), only relatively few have hitherto been widely used industrially, with 1,4-diazabicyclo[2,2,2]octane, bis(2-dimethylaminoethyl) ether, triethylamine, dimethylcyclohexylamine, dimethylethanolamine, dimethylbenzylamine, methylmorpholine, and ethylmorpholine, being the most important. One would, of course, mainly use those catalysts which are distinguished by high activity, economical method of preparation, and breadth of application.

Another increasingly important consideration is the toxicological evaluation of the catalysts with regard to their safety in use and freedom from odor. Many of the amine catalysts used today, such as DABCO or triethylamine, may be regarded as unsatisfactory in this respect because of their high volatility and relatively intense amine odor that persists in the end product produced with the aid of such catalysts. In view of the many possible applications of polyurethane resins, it is equally desirable to provide "tailor-made" catalysts adapted to the individual requirements. One possibility lies in chemically modifying a type of catalyst to adjust its activity to its particular purpose.

It has now surprisingly been found that certain pyrrolidine derivatives can advantageously be used as catalysts for the preparation of polyurethanes. Compared with the above-mentioned amine catalysts, the compounds according to the invention have a comparable or even higher activity. Another welcome effect of the catalysts according to the invention is that the activity of the products can be adjusted exactly as required by suitable choice of the substituents on the ring, in contrast to, for example, DABCO, which allows no variation within economically acceptable limits. Another advantage of the catalysts of the invention is the very faint odor and low volatility of the compounds, which are in part bound in the polymer by isocyanate-reactive groups so that the odor is considerably reduced in the preparation of polyurethane products. Other advantages may also be observed, including, for example, the ease of handling (because the pyrrolidines that are preferably used are liquid), the advantageous rate of hardening, and, not least, the very simple method by which some of these compounds may be prepared.

SUMMARY OF THE INVENTION

The present invention thus relates to a process for preparing polyisocyanate polyaddition products comprising reacting
(a) polyisocyanates with
(b) relatively high molecular weight compounds containing at least two isocyanate-reactive hydrogen atoms and
(c) optionally, chain-extending agents,
in the presence of
(d) 3,(4)-substituted pyrrolidine catalysts corresponding to formula (I)

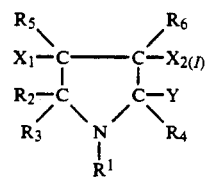

wherein
$R_1$ denotes hydrogen, a $C_1$–$C_{12}$-alkyl group, or an optionally alkyl-substituted $C_3$–$C_7$-cycloalkyl, $C_6$–$C_{14}$-aryl, or -aralkyl group (with the proviso that each $R_1$ may contain N or O atoms): or $R_1$ denotes
  (i) together with $R_4$ an optionally substituted $C_1$–$C_5$-alkylene group or
  (ii) a $C_1$–$C_6$-alkylene group connecting two pyrrolidine groups of formula (I) through the two ring nitrogen atom;

$R_2$ and $R_3$ independently denote hydrogen, a $C_1$–$C_{12}$-alkyl group or an optionally alkyl-substituted $C_3$–$C_7$-cycloalkyl, $C_6$–$C_{14}$-aryl, or -arylalkyl group; or $R_2$ and $R_3$ together denote an optionally alkyl-substituted $C_2$–$C_9$-alkylene group;

$R_4$ denotes hydrogen, a $C_1$–$C_{12}$-alkyl group, or an optionally alkyl-substituted $C_3$–$C_7$-cycloalkyl, $C_6$–$C_{14}$-aryl, or -arylalkyl group; or $R_4$ together with $R_1$ denotes an optionally substituted $C_1$–$C_5$-alkylene group;

$R_5$ and $R_6$ independently denote hydrogen, a $C_1$–$C_{12}$-alkyl group or an optionally alkyl-substituted $C_3$–$C_7$-cycloalkyl, $C_6$–$C_{14}$-aryl, or -arylalkyl group; or $R_5$ and $R_6$ together denote a group having the structure

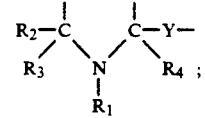

$X_1$ and $X_2$ independently denote (i.e., they may be identical or different) hydrogen, carboxylic acid groups or functional derivatives thereof (such as esters or amides) optionally containing O or N atoms, nitrile, or $CHR_7OH$, $CH_2NR_8R_9$, $CONR_8R_9$, or $NR_8R_9$ groups, in which $R_7$ represents hydrogen, a $C_1$-$C_{12}$-alkyl group, or an optionally alkyl-substituted -cycloalkyl, -aryl or arylalkyl group, and $R_8$ and $R_9$ independently denote hydrogen, a $C_1$-$C_{12}$-alkyl group or an optionally alkyl-substituted -cycloalkyl, -aryl, or -arylalkyl group; and Y denotes hydrogen, a carboxylic acid group or a functional derivative thereof (such as an ester or amide) optionally containing O or N atoms, nitrile, or a $CHR_7OH$ or $CH_2NR_8R_9$ group, in which $R_7$, $R_8$, and $R_9$ are defined as above;

with the provisos that (1) at least one of the groups $X_1$ or $X_2$ must be other than hydrogen and (2) when $X_1$ and $X_2$ are not identical, the compounds may be mixtures of different isomers with respect to the position of the substituents $X_1$ and $X_2$ in the 3- or 4-position of the pyrrolidine ring, different stereoisomers, or isomer pure compounds;

(e) optionally, other known catalysts, and (f) other known additives.

The present invention further relates to a process for preparing 3,(4)-substituted pyrrolidine catalyst of formula (V)

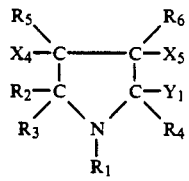 (V)

wherein $R_1$ denotes hydrogen, a $C_1$-$C_{12}$-alkyl group, on an optionally alkyl-substituted $C_3$-$C_7$-cycloalkyl, aryl, or aralkyl group (with the proviso that each $R_1$ may contain N or O atoms); or $R_1$ denotes (i) together with $R_4$ an optionally substituted $C_1$-$C_5$-alkylene group or (ii) a $C_1$-$C_6$-alkylene group connecting two pyrrolidines of formula (V) through the two ring nitrogen atoms;

$R_2$ and $R_3$ independently denote hydrogen, a $C_1$14 $C_{12}$-alkyl group or an optionally alkyl-substituted cycloalkyl, aryl, or arylalkyl group; or $R_2$ and $R_3$ together denote an optionally alkyl-substituted $C_2$-$C_9$-alkylene group;

$R_4$ denotes hydrogen, a $C_1$-$C_{12}$-alkyl group, or an optionally alkyl-substituted $C_3$-$C_7$- cycloalkyl, aryl, or arylalkyl group; or $R_4$ together with $R_1$ denote an optionally substituted $C_1$-$C_5$-alkylene group;

$R_5$ and $R_6$ independently denote hydrogen, a $C_1$-$C_{12}$-alkyl group or an optionally alkyl-substituted cycloalkyl, aryl, or arylalkyl group; or R and R together denote a group having the structure

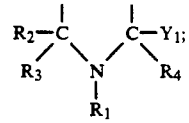

$X_4$ and $X_5$ independently denote hydrogen, carboxylic acid groups or functional derivatives thereof (such as esters or amides) optionally containing O or N atoms, nitrile, or $NO_2$; and $Y_1$ denotes hydrogen (formed when Z, below, is a carboxylic acid group —COOH), a carboxylic acid group or a functional derivative thereof (such as an ester or amide) optionally containing 0 or N atoms, or nitrile;

comprising reacting, at an elevated temperature in an inert solvent (preferably with azeotropic removal of water), (a) α-aminocarboxylic acid derivatives of formula (II)

$$R_1NH-CHR_4-Z \qquad (II)$$

wherein $R_1$ denotes hydrogen, a $C_1$-$C_{12}$-alkyl group, or an optionally alkyl-substituted $C_3$-$C_7$-cycloalkyl, aryl, or aralkyl group (with the proviso that each $R_1$ may contain N or O atoms); or $R_1$ denotes (i) together with $R_4$ an optionally substituted $C_1$-$C_5$-alkylene group or (ii) a $C_1$-$C_6$-alkylene group connecting two α-aminocarboxylic acid derivative of formula (II) through the α-amino nitrogen atom;

$R_4$ is defined as above; and

Z denotes a carboxylic acid group or a functional derivative thereof (such as an ester or amide) optionally containing O or N atoms, or nitrile;

with (b) ketones or aldehydes of formula (III)

$$R_2R_3C=O \qquad (III)$$

wherein $R_2$ and $R_3$ are defined as above; and (c) activated olefins of formula (IV)

$$X_4R_{10}C=CR_{11}X_5 \qquad (IV)$$

wherein $X_4$ and $X_5$ are defined as above; and $R_{10}$ and $R_{11}$ independently denote hydrogen, a $C_1$-$C_{12}$-alkyl group or an optionally alkyl-substituted cycloalkyl, aryl, or arylalkyl group; or when $R_5$ and $R_5$ together denote a group having the formula

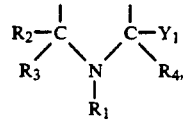

$R_{10}$ and $R_{11}$ together form a third bond (such that compound of formula (IV) is an acetylene of formula $R_{10}C\equiv CR_{11}$);

with the proviso that the ketone or aldehyde is added continuously or in portions at the rate at which the reaction progresses.

DETAILED DESCRIPTION OF THE INVENTION

Preferred catalysts of the invention are compounds corresponding to the formula (Ia)

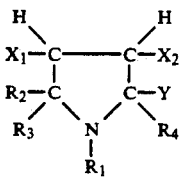

(Ia)

wherein
$R_1$, $R_2$, $R_3$, and $R_4$ have the meanings given for formula (I);
$X_1$ and $X_2$ independently denote hydrogen, a carboxylic acid ester or amide group optionally containing O or N atoms, nitrile, or a $CH_2OH$ or $CH_2NH_2$ group; and
Y denotes hydrogen or a $CH_2OH$ or $CH_2NH_2$ group.

Particularly preferred catalysts are those corresponding to the formula (Ib)

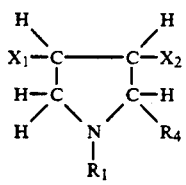

(Ib)

wherein
$X_1$ and $X_2$ have the meanings given for formula (Ia);
$R_1$ denotes a $C_1$-$C_{12}$-alkyl group or an optionally alkyl-substituted $C_5$-$C_6$-cycloalkyl, aryl, or arylalkyl group, or $R_1$ together with $R_4$ denote an optionally substituted $C_3$-$C_5$-alkylene group; and
$R_4$ denotes hydrogen, or $R_4$ together with $R_1$ denote an optionally substituted $C_3$-$C_5$-alkylene group.

Also preferred as catalysts of the invention are new compounds corresponding to the general formula (Ic)

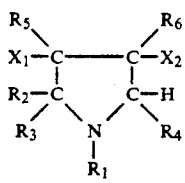

(Ic)

wherein
$R_1$, $R_2$, and $R_3$ independently denote hydrogen, a $C_1$-$C_{12}$-alkyl group or an optionally alkyl-substituted cycloalkyl, acyl, or aralkyl group;
at least one of $R_5$ or $R_6$ denotes hydrogen, with the other of $R_5$ or $R_6$ having the meanings given in formula (I);
one of $X_1$ or $X_2$ denotes hydrogen and the other of $X_1$ or $X_2$ denotes a $CH_2NH_2$, $CH_2OH$, CN, or $CONR_8R_9$ group; and
$R_4$, $R_8$, and $R_9$ have the meanings given in formula (I); with the proviso that when $R_1$ is hydrogen or methyl (and optionally $R_9$ is methyl), at least one of the groups $R_2$, $R_3$, $R_4$, and $R_5$ or $R_6$ is not hydrogen; and the isomeric mixtures thereof formed by the exchange of $X_1$ and $X_2$.

New compounds corresponding to the formula (Id) are also preferred as catalysts of the invention:

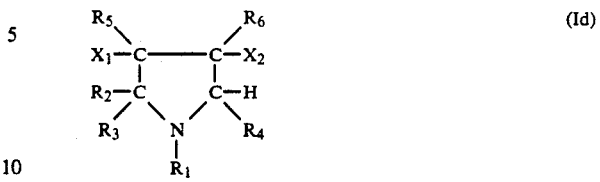

(Id)

wherein
$R_2$, $R_3$, $R_5$, $R_6$, $X_1$, and $X_2$ have the meanings given in formula (I); and
$R_1$ together with $R_4$ denote an optionally substituted $C_2$-$C_4$-alkylene group;
with the proviso that at least one of the groups $R_2$, $R_2$, $R_3$, $R_5$, or $R_6$ is not hydrogen if one of $X_1$ or $X_2$ is hydrogen and the other of $X_1$ or $X_2$ is $COOCH_3$ or $COOC_2H_5$.

The pyrrolidines according to the invention are prepared from readily available and inexpensive starting materials such as amino acid derivatives, ketones or aldehydes, and olefins by a very simple method, the main stages of which are described e.g. in *Bull. Soc. Chim. France*, 1988, pages 579-583 or in *Bull. Chem. Soc. Japan*, 60, pages 4079-4090 (1989). The described process, however, requires very low concentrations (less than 0.1 mol/l, preferably about 0.04 mol/l) for obtaining high yields (see *Bull. Soc. Chim. France*, article at page 581, top of right column). Consequently, the quantities of solvent required are not acceptable for an economical method of production. If the process described is carried out at higher concentrations (for example, 1 mol/l), the yields of the required compounds fall drastically to below 30% in favor of insoluble, undistillable inactive resins. Even at a higher dilution of from 0.1 to 0.2 mol/l, the yields are not economically acceptable. Substituted pyrrolidines cannot be used on an industrial scale by this process.

It has now been found that very high yields are obtained even when substantially higher and, therefore, economical concentrations are used if the ketone or aldehyde component is added slowly in the course of the reaction. The progress of the reaction, and hence the rate at which the components should be added, can easily be ascertained by gas chromatography or by determining the quantity of the water of reaction formed.

The present invention therefore also relates to a process for the preparation of pyrrolidines of formula (I) that are substituted in the 3- and/or 4-position by the reaction at elevated temperature in an inert solvent (preferably with azeotropic removal of the water of reaction) of α-aminocarboxylic acid derivatives of formula (II) with ketones or aldehydes of formula (III) and activated olefins of formula (IV) to form compounds corresponding to formula (V) in accordance with the following Scheme A.

Scheme A

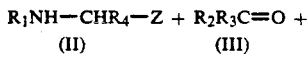

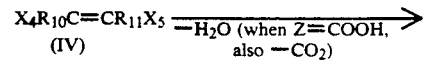

-continued
Scheme A

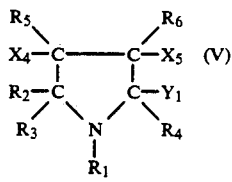

wherein
- $R_1$ denotes hydrogen, a $C_1$–$C_{12}$-alkyl group, or an optionally alkyl-substituted $C_3$–$C_7$-cycloalkyl, aryl, or aralkyl group (with the proviso that each $R_1$ may contain N or O atoms); or $R_1$ denotes (i) together with $R_4$ an optionally substituted $C_1$–$C_5$-alkylene group or (ii) a $C_1$–$C_6$-alkylene group connecting two α-aminocarboxyoic acid derivative of formula (II) through the α-amino nitrogen atom or connecting two pyrrolidines of formula (V) through the two ring nitrogen atoms;
- $R_2$ and $R_3$ independently denote hydrogen, a $C_1$–$C_{12}$-alkyl group or an optionally alkyl-substituted cycloalkyl, aryl, or arylalkyl group; or $R_2$ and $R_3$ together denote an optionally alkyl-substituted $C_1$–$C_9$-alkylene group;
- $R_4$ denotes hydrogen, a $C_1$–$C_{12}$-alkyl group, or an optionally alkyl-substituted $C_3$–$C_7$-cycloalkyl, aryl, or arylalkyl group; or $R_4$ together with $R_1$ denote an optionally substituted $C_1$–$C_5$-alkylene group;
- $R_5$ and $R_6$ independently denote groups having the meanings defined for $R_2$ and $R_3$ or together denote a group having the structure

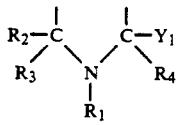

- $R_{10}$ and $R_{11}$ independently denote groups having the meanings defined for $R_2$ and $R_3$ or, when $R_5$ and $R_6$ together denote the structure shown above, $R_{10}$ and $R_{11}$ may together form a third bond (such that compound of formula (IV) is an acetylene of formula $R_{10}C\equiv CR_{11}$);
- $X_4$ and $X_5$ independently denote hydrogen, carboxylic acid groups or functional derivatives thereof (such as esters or amides) optionally containing O or N atoms, nitrile, or $NO_2$; and
- Z denotes a carboxylic acid group or a functional derivative thereof (such as an ester or amide) optionally containing O or N atoms, or nitrile;
- $Y_1$ is identical to Z or denotes hydrogen when Z is a carboxylic acid group —COOH;

The ketone or aldehyde is added continuously or portionwise at the same rate at which the reaction progresses. After isolation of product (V), functional groups $X_4$, $X_5$, and/or $Y_1$ of compound (V) can optionally be transformed in known manner into compounds having the broader range of meanings of $X_1$, $X_2$, and/or Y of formula (I).

Due to the gradual addition of ketone or aldehyde in accordance with the invention, the end product is obtained at concentrations in the reaction solution of at least 0.2 mol per liter. The concentration of the end product obtained is most preferably from 0.5 to 2 mol/l.

Examples of suitable α-aminocarboxylic acid derivatives of formula (II) include α-amino acids such as glycine, N-methylglycine (sarcosine), N-phenylglycine, N-benzylglycine, N-triphenylmethylglycine, alanine, N-methylalanine, N-phenylalanine, lysine, N-methyllysine, methionine, N-methylmethionine, 2-aminomalonic acid, 2-methylaminosuccinic acid; cyclic amino acids such as proline or piperidine-2-carboxylic acid; the methyl or ethyl esters of the above-mentioned amino acids; or a-aminonitriles such as 2-aminoacetonitrile or 2-N-methylaminoacetonitrile. N-Methylglycine and proline are particularly preferred.

Examples of suitable ketones of formula (III) include acetone, methyl ethyl ketone, 2-pentanone, 3-pentanone, methyl isopropyl ketone, 4-heptanone, methyl nonyl ketone, dinonyl ketone, cyclohexanone, methyl cyclohexanone, cyclopentanone, acetophenone, 4-chloroacetophenone, and benzophenone. Examples of suitable aldehydes of formula (III) include formaldehyde and its derivatives such as trioxane, paraformaldehyde, and dimethoxymethane, acetaldehyde, butyraldehyde, isobutyraldehyde, pivalic aldehyde, oenanthic aldehyde, 2-ethylhexanal, benzaldehyde, 3-methylbenzaldehyde, propiophenone, and 3-phenylpropionaldehyde. Formaldehyde and paraformaldehyde are particularly preferred.

Activated olefins of formula (IV) are to be understood to include olefins having at least one activating group $X_4$ or $X_5$ within the above definition in conjugation with the double or triple bond. Suitable activating olefins include acrylic acid, methacrylic acid, crotonic acid, 3-methylcrotonic acid, sorbic acid, fumaric acid, maleic acid, itaconic acid, cinnamic acid, acetylene dicarboxylic acid, as well as the methyl, ethyl, and butyl esters of the above-mentioned acids, acrylonitrile, methacrylonitrile, and acetylene dicarboxylic acid dinitrile. When acetylenes are used instead of olefins (VI) (that is, when $R_{10}$ and $R_{11}$ together are a third bond), bicyclo-3,7-diazaoctane derivatives are obtained. The methyl, ethyl, and butyl esters of acrylic acid, the methyl and ethyl esters of maleic acid, and acrylonitrile are particularly preferred.

Among the inert solvents used to prepare the pyrrolidines of the invention, those having a boiling point above about 70° C. are preferred. The starting materials for the reaction may be dissolved or suspended in the solvents. The use of a solvent may be omitted and an excess of the olefin component used as solvent instead. Nearly all industrially used solvents, with the exception of ketones and water, are inert in the reaction and only a few examples will therefore be mentioned, including petroleum ether, petroleum hydrocarbons, benzene, toluene, xylenes, chlorobenzene, dichlorobenzenes, anisole, ethanol, isopropanol, butanol, dioxane, dimethylformamide, and dimethylacetamide, as well as mixtures of the aforesaid solvents. Toluene and dimethylformamide and mixtures thereof are particularly preferred.

In a preferred embodiment, the water of reaction is removed azeotropically. This water, however, may be left in the reaction mixture, for example, when dimethylformamide is used, or may be removed by some other means, such as by using known inert dehydrating agents such as molecular sieves, or by distilling without using an azeotropic mixture.

Many products obtainable according to Scheme A are already highly active catalysts. Activity may, however, be enhanced by transforming the functional groups $X_4$, $X_5$, and $Y_1$ into groups having the extended range of meanings of $X_1$, $X_2$, and $Y$ of formula (I) by simple methods known in the art. Such methods include, for example, aminolysis with primary or secondary amines optionally containing N or O atoms; transesterification with alcohols optionally containing N or O atoms; or reduction. The incorporable examples of compounds containing isocyanate-reactive groups in particular may be obtained by these means.

The following scheme of formulas represents by way of example a specific reaction sequence to illustrate the process:

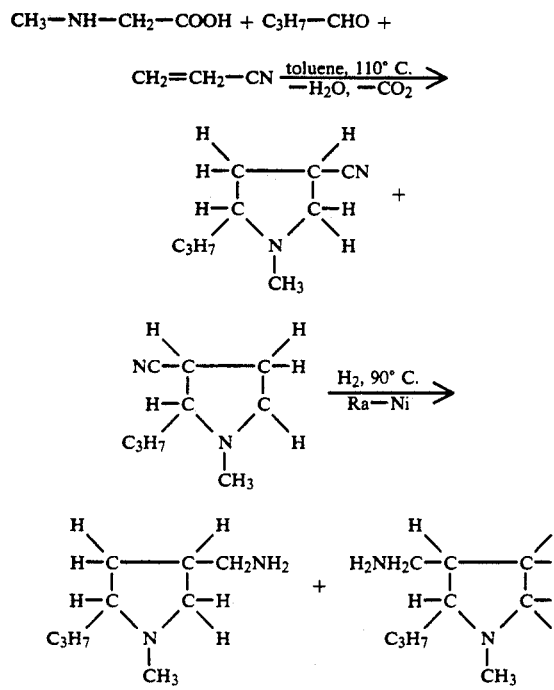

The following are examples of preferred catalysts according to the invention: 3-hydroxymethyl-N-methylpyrrolidine, 3,4-bis(hydroxymethyl)-N-methylpyrrolidine, 3-aminomethyl-N-methylpyrrolidine, N-methylpyrrolidine-3-carboxylic acid N-(3-dimethylaminopropyl)amide, 1-azabicyclo[3.3.0]octane-3-carboxylic acid butyl ester, I-azabicyclo[3.3.0]octane-4-carboxylic acid butyl ester, I-azabicyclo[4.3.0]nonane-3-carboxylic acid butyl ester, I-azabicyclo[4.3.0]nonane-4-carboxylic acid butyl ester, 3-cyano-1-azabicyclo[3.3.0]octane, 4-cyano-1-azabicyclo[3.3.0]octane, 3-aminomethyl-1-azabicyclo[3.3.0]octane and 4-aminomethyl-1-azabicyclo[3.3.0]octane. Particularly preferred catalysts include 3-hydroxymethyl-N-methylpyrrolidine, 3,4-bis(hydroxymethyl)-N-methylpyrrolidine, 3-aminomethyl-N-methylpyrrolidine, N-methylpyrrolidine-3-carboxylic acid N-(3-dimethylaminopropyl)amide, 1-azabicyclo-[3.3.0]octane-3-carboxylic acid butyl ester, 1-azabicyclo[3.3.0]octane-4-carboxylic acid butyl ester; 3-aminomethyl-1-azabicyclo[3.3.0]octane, and 4-aminomethyl-1-azabicyclo[3.3.0]-octane.

The catalysts according to the invention are colorless to slightly yellowish compounds, the preferred types being liquid, and are soluble in organic solvents and soluble or dispersible in water.

When preparing optionally cellular synthetic resins by the polyisocyanate polyaddition process according to the invention, the new catalysts are preferably used in quantities of from 0.01 to 5% by weight, based on the compound containing active hydrogen atoms. A larger quantity than that mentioned above may be used but has no advantage. When using the catalysts of the invention in combination with conventional catalysts normally used in polyurethane chemistry, the proportion of catalysts corresponding to formula (I) should preferably amount to at least 50% by weight of the total quantity of catalysts used.

The isocyanate-reactive compounds which are used as component (b) in the process according to the invention are those used in previously known processes for the preparation of polyurethanes and are described, for example, in Kunststaffhandbuch, Vol. VII, Polyurethane, Hansen-Verlag, Munich (1983) or in Houben-Weyl, Makromalekulare Stoffe, Vol. E20, having a molecular weight of 300–10000, preferably 1000–6000.

The compounds containing NCO groups used as component (a) according to the invention are the same compounds as those used in previously known processes and are described, for example, in Kunststoffhandbuch, Vol. VII, Polyurethane, Hansen-Verlag, Munich (1983) or in Houben-Weyl, Makromolekulare Stoffe, Vol. E20.

When carrying out the process according to the invention, the substituted pyrrolidines are used in the same way as the previously known catalysts. For example, the catalyst may be used in liquid form or may be dissolved in a polyol or a suitable solvent. The catalyst may be used at any temperature or other conditions, either alone or in combination with other known catalysts that are suitable for the preparation of polyurethanes. Suitable other catalysts include organic or inorganic tin compounds or other organometallic compounds; tertiary amines, alkanolamines, cyclic amines, polyamines, and the like; alkali metal compounds; and other co-catalysts.

The process for preparing polyisocyanate addition products according to the invention is suitable for the conventional methods of preparation, such as the one-shot or prepolymer process for the preparation of polyurethane foams, polyurethane elastomers, polyurethane coatings, and the like, as well as for the crosslinking reaction that is frequently required after direct polyaddition. All other conditions are the same as in conventional urethane polyaddition processes. Further additives, such as known chain lengthening agents, blowing agents, foam stabilizers, emulsifiers, paints, pigments, and fillers may also be used.

The above-mentioned catalysts of the invention accelerate the polyaddition reaction to a considerable extent so that the quantity of catalyst required is very small. Because the catalyst compounds according to the invention have only a faint odor and are not volatile liquids or solids or incorporable compounds, the polyurethane products obtained are free from unwanted odors.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all parts and percentages are parts by weight and percentages by weight, respectively.

EXAMPLES

Example 1. Preparation of 3-cyano-N-methylpyrrolidine and of 3-aminomethyl-N-methylpyrrolidine a) Comparison Example (Process Not According to the Invention)

A mixture of 300 g of N-methylglycine, 300 g of acrylonitrile, 105 g of paraformaldehyde, and 3 liters of toluene was introduced into a 4-liter three-neck flask equipped with stirrer, reflux condenser, and a water separator having a capacity of about 70 ml. The mixture was heated at vigorous reflux at a bath temperature of from 120° to 140° C. until the evolution of water ceased. A brownish yellow solution from which a dark brown resin had separated was obtained at the end of the reaction. The solvent was distilled off and the residue was fractionated under vacuum to yield 96 g (26% of theoretical) of 3-cyano-N-methylpyrrolidine.

b) Comparison Example (Process Not According to the Invention)

A mixture of 50 g of N-methylglycine, 60 g of acrylonitrile, 25 g of paraformaldehyde, and 3 liters of toluene was introduced into a 4-liter three-neck flask equipped with stirrer, reflux condenser, and a water separator having a capacity of about 70 ml. The mixture was heated at vigorous reflux at a bath temperature of 120° to 140° C. until the evolution of water ceased. A brownish yellow solution was obtained at the end of the reaction. The solvent was distilled off and the residue was fractionated under vacuum to yield 32 g (51% of theoretical) of 3-cyano-N-methylpyrrolidine.

c) Process According to the Invention

A mixture of 300 g of N-methylglycine, 300 g of acrylonitrile, and 3 liters of toluene was introduced into a 4-liter three-necked flask equipped with stirrer, reflux condenser, dosing funnel, and a water separator having a capacity of about 70 ml. The mixture was heated at vigorous reflux at a bath temperature of from 120° to 140° C. A total of 105 g of paraformaldehyde was then added in portions of 3 g, with no portions being added until the evolution of water from the previous addition has ceased. A homogeneous, slightly yellowish solution was obtained at the end of the reaction. The solvent was distilled off and the residue was fractionated under vacuum to yield 315 g (85% of theoretical) of 3-cyano-N-methylpyrrolidine (b.p. 83°–85° C., 22 Mm Hg).

The subsequent reduction to 3-aminomethyl-N-methylpyrrolidine was carried out by a known process as follows. The cyano compound was dissolved in an equal volume of methanol. After the resultant solution was introduced into a 2 liter autoclave, 20 g of Raney cobalt was added and 130 g of ammonia was forced in. Hydrogenation was then carried out at 90° C. under a hydrogen pressure of from 90 to 100 bar for about 3 hours. The solution was depressurized, filtered, and concentrated by evaporation. The resultant residue was fractionated under vacuum to yield 310 g (95% of theoretical) of 3-aminomethyl-N-methylpyrrolidine (b.p. 61° C., 22 mbar).

Examples 2 to 9

The compounds whose formulas are shown below were prepared by the process described in Example 1c) under the same conditions.

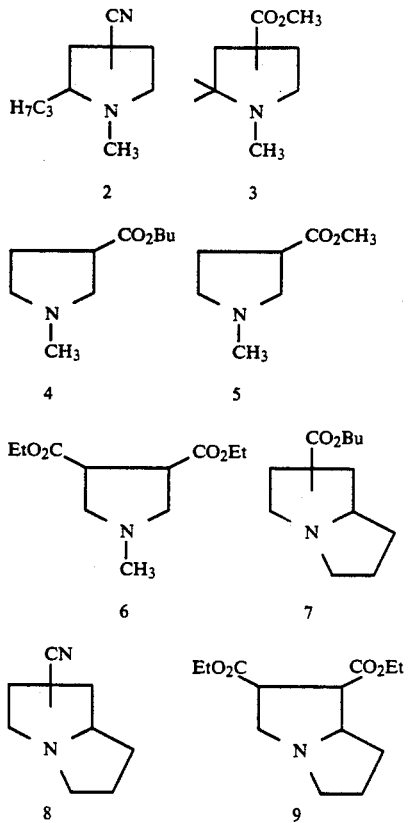

Table 1 shows the starting materials and the yields obtained (% of theoretical, based on the amino acid derivative) after purification by distillation.

TABLE 1

| Example | Amino acid derivative | Ketone/ aldehyde | Olefin | Yield |
| --- | --- | --- | --- | --- |
| 2 | Methyl glycine | Butyraldehyde | Acrylonitrile | 87% |
| 3 | Methyl glycine | Acetone | Methyl acrylate | 79% |
| 4 | Methyl glycine | Paraformaldehyde | Butyl acrylate | 89% |
| 5 | Methyl glycine | Paraformaldehyde | Methyl acrylate | 81% |
| 6 | Methyl glycine | Paraformaldehyde | Diethyl maleate | 85% |
| 7 | DL-proline | Paraformaldehyde | Butyl acrylate | 95% |
| 8 | DL-proline | Paraformaldehyde | Acrylonitrile | 92% |
| 9 | DL-proline | Paraformaldehyde | Diethyl maleate | 90% |

Physical data of compounds of Examples 2 to 9:
2: b.p. 103–110° C. (20 mbar)
3 (2 Isomers): b.p. 75–78° C. (11 mbar)
4: b.p. 105° C. (12 mbar)
5: b.p. 71° C. (12 mbar)
6 (2 Isomers): b.p. 140–145° C. (11 mbar)
7 (4 Isomers): b.p. 140–147° C. (12 mbar)
8 (4 Isomers): b.p. 115–120° C. (22 mbar)
9 (6 Isomers): b.p. 175–185° C. (10 mbar)

Examples 10 to 14

The compounds of Examples 2 and 8 were hydrogenated to compounds 10 and 11 by the process described in Example 1a). The compounds of Examples 5 and 6 were reduced to compounds 12 and 13 by the known process of reduction with sodium boron hydride. The compound of Example 5 was converted into compound 14 by the known process of aminolysis with 1-amino-3-dimethylaminopropane. These compounds have the following formulas:

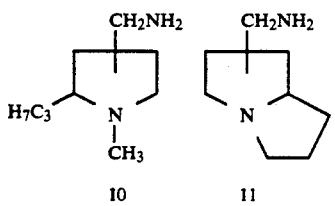

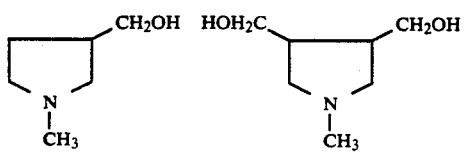

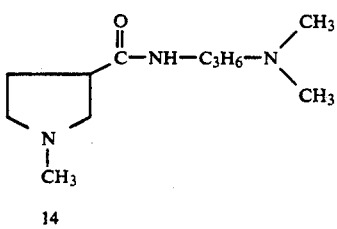

Example 15

This example shows the high catalytic activity of two examples from the series of 3-substituted pyrrolidines in a flexible foam system. A 1:1 mixture of 1-azabicyclo[3,3,0]octane-3- and -4-carboxylic acid butyl ester (Catalyst 1) and 3-aminomethyl-N-methylpyrrolidine (catalyst 2) prepared by the process described in the text (see Examples 7 and 1c), respectively) were used.

| A-Component: | |
|---|---|
| 18 parts | a mixture of 2,4-toluene diisocyanate and 2,6-toluene diisocyanate in a ratio of 80:20 |
| B-Component: | |
| 50.00 parts | a polyether polyol with OH number 35 mg KOH/g prepared by the reaction of trimethylolpropane with propylene oxide (PO) followed by reaction with ethylene oxide (EO) at a PO/EO ratio of 86.55/13.45 |
| 1.50 parts | water |
| 0.50 parts | a polyether polysiloxane as stabilizer (Stabilizer OS 50 of Bayer AG) |
| 0.3 parts | pyrrolidine catalyst 1 or 2 described above |

The A-Component was combined with the B-Component and the two were thoroughly mixed using a high speed stirrer for 10 seconds. The reaction mixture was then foamed in an open mold at room temperature.

| | Cream time | Rise time |
|---|---|---|
| Catalyst 1 | 4 sec | 90 sec |
| Catalyst 2 | 4 sec | 90 sec |

Example 16 to 20

These examples show the high catalytic activity (which can be graded) of other examples from the series of 3-substituted pyrrolidine in a polyurethane cold flexible foam system.

The following catalysts prepared according to the text were used:
Catalyst 1: see Example 15
Catalyst 2: see Example 15
Catalyst 3: N-methylpyrrolidine-3-carboxylic acid butyl ester (see Example 4)
Catalyst 4: N-methylpyrrolidine-3-carboxylic acid N-(3-dimethylaminopropyl)amide (see Example 14)

| A-Component: | |
|---|---|
| 37 parts | a mixture of 80% by weight 2,4-toluene diisocyanate and 2,6-toluene diisocyanate (in a ratio of 80:20) and 20% 4,4'-diisocyanato-diphenylmethane with polymeric constituents having an isocyanate content of 44.5% ± 0.5% by weight (Trade Product Desmodur ® VT 06 of Bayer AG) |
| B-Component: | |
| 100.00 parts | a polyether polyol with OH number 28 ± 2 mg KOH/g prepared by the reaction of trimethylolpropane (TMP) with propylene oxide (PO) followed by a reaction with ethylene oxide (EO) at a PO/EO ratio of 82/18 |
| 3.00 parts | water |
| 0.05 parts | a 70% solution of bis(2-dimethylaminoethyl) ether in dipropylene glycol (DPG) |
| 0.25 parts | a 33% solution of diazabicyclo[2.2.2]octane (DABCO) in DPG |
| 0.20 parts | foam stabilizer B4617 (Goldschmidt AG) |
| 0.80 parts | a polyether polysiloxane as stabilizer (Stabilizer OS 50 of Bayer AG) |
| 0.6 parts | pyrrolidine catalysts 1 to 4 described above |

The component were foamed as in Example 15. The results obtained when using the various catalysts are summarized in Table 2.

TABLE 2

| Example | Catalyst | Cream time [sec] | Gel time [sec] | Rise time [sec] |
|---|---|---|---|---|
| 16 | none | 9 | 108 | 213 |
| 17 | 1 | 5 | 46 | 93 |
| 18 | 2 | 4 | 38 | 72 |
| 19 | 3 | 6 | 83 | 120 |
| 20 | 4 | 5 | 61 | 113 |

The foams obtained exhibited perfect foam structure.
What is claimed is:
1. A process or preparing 3,(4)-substituted pyrrolidine catalysts of the formula

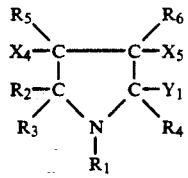

wherein
$R_1$ denotes hydrogen, a $C_1$-$C_{12}$-alkyl group, or an optionally alkyl-substituted $C_3$-$C_7$-cycloalkyl, aryl, or aralkyl group (with the proviso that each $R_1$ may contain N or O atoms); or $R_1$ denotes (i) together with $R_4$ an optionally substituted $C_1$-$C_5$-alkylene group or (ii) a $C_1$-$C_6$-alkylene group connecting two pyrrolidine through the two ring nitrogen atoms;

$R_2$ and $R_3$ independently denote hydroen, a $C_1$-$C_{12}$-alkyl group or an optionally alkyl-substituted cycloalkyl, aryl, or arylalkyl group; or $R_2$ and $R_3$ together denote an optionally alkyl-substituted $C_1$-$C_9$-alkylene group;

$R_4$ denotes hydrogen, a $C_1$-$C_{12}$-alkyl group, or an optionally alkyl-substituted $C_3$-$C_7$-cycloalkyl, aryl, or arylalkyl group; or $R_4$ together with $R_1$ denote an optionally substituted $C_1$-$C_5$-alkylene group;

$R_5$ and $R_6$ independently denote hydrogen, a $C_1$-$C_{12}$-alkyl group or an optionally alkyl-substituted cycloalkyl, aryl, or arylalkyl group; or $R_5$ and $R_6$ together denote a group having the structure

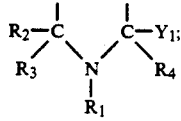

$X_4$ and $X_5$ independently denote hydrogen, carboxylic acid groups or ester or amide derivatives thereof, nitrile, or $NO_2$; and $Y_1$ denotes hydrogen, a carboxylic acid ester or amide derivative, or nitrile;

comprising reacting, at an elevated temperature in an inert solvent, optionally with azeotropic removal of water, (a) an α-aminocarboxylic acid derivative of the formula

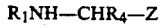

wherein $R_2$ denotes hydrogen, a $C_1$-$C_{12}$-alkyl group, or an optionally alkyl-substituted $C_3$-$C_7$-cycloalkyl, aryl, or an aralkyl group (with the proviso that each $R_1$ may contain N or O atoms); or $R_1$ denotes (i) together with $R_4$ an optionally substituted $C_1$-$C_5$-alkylene group or (ii) a $C_1$-$C_6$-alkylene group connecting two α-aminocarboxylic acid derivatives through the α-amino nitrogen atom;

$R_4$ is defined as above; and

Z denotes a carboxylic acid group or an ester or amide derivative thereof, or nitrile;

with (b) a ketone or aldehyde of the formula

wherein $R_2$ and $R_3$ are defined as above; and (c) an activated olefin of the formula

wherein $X_4$ and $X_5$ are defined as above; and $R_{10}$ and $R_{11}$ independently denote hydrogen, a $C_1$-$C_{12}$-alkyl group or an optionally alkyl-substituted cycloalkyl, aryl, or arylalkyl group; or $R_{10}$ and $R_{11}$ together form a third bond when $R_5$ and $R_6$ of the 3(4)-substituted pyrrolidine catalyst together denote a group having the formula

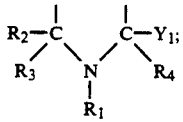

with the proviso that the ketone or aldehyde is added continuously or in portions at the rate at which the reaction progresses.

* * * * *